(12) United States Patent
Liu et al.

(10) Patent No.: US 8,709,700 B2
(45) Date of Patent: Apr. 29, 2014

(54) FLUORINE-FREE FUSED RING HETEROAROMATIC PHOTOACID GENERATORS AND RESIST COMPOSITIONS CONTAINING THE SAME

(75) Inventors: Sen Liu, Hopewell Junction, NY (US); Pushkara R. Varanasi, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 33 days.

(21) Appl. No.: 13/614,575

(22) Filed: Sep. 13, 2012

(65) Prior Publication Data
US 2013/0011788 A1    Jan. 10, 2013

Related U.S. Application Data

(62) Division of application No. 12/692,961, filed on Jan. 25, 2010, now Pat. No. 8,343,706.

(51) Int. Cl.
*G03F 7/004* (2006.01)
*G03F 7/26* (2006.01)
*C07D 263/54* (2006.01)
*C07C 309/25* (2006.01)
*C07C 309/26* (2006.01)

(52) U.S. Cl.
CPC ............. *G03F 7/004* (2013.01); *Y10S 430/121* (2013.01); *Y10S 430/122* (2013.01); *Y10S 430/126* (2013.01)
USPC ........ 430/270.1; 430/326; 430/313; 430/920; 430/921; 430/925; 548/246; 568/22

(58) Field of Classification Search
CPC .. C07D 263/54; C07C 309/25; C07C 309/26; G03F 7/004; G03F 7/028; G03F 7/029; G03F 7/26
USPC .............. 430/270.1, 313, 326, 919, 920, 921, 430/925; 548/246; 568/22, 23, 24, 25, 27, 568/28, 30
See application file for complete search history.

(56) References Cited

U.S. PATENT DOCUMENTS

| 3,775,367 | A | 11/1973 | Nouvertne |
| 4,039,509 | A | 8/1977 | Mark |
| 6,440,634 | B1 | 8/2002 | Ohsawa et al. |
| 6,482,567 | B1 | 11/2002 | Cameron et al. |
| 7,297,616 | B2 | 11/2007 | Cameron et al. |
| 8,330,039 | B2 * | 12/2012 | Smith et al. .................... 136/254 |
| 2003/0050477 | A1 * | 3/2003 | Zagar et al. ................ 546/271.7 |
| 2003/0109608 | A1 | 6/2003 | Worku et al. |
| 2009/0176173 | A1 | 7/2009 | Glodde et al. |
| 2009/0181319 | A1 | 7/2009 | Li et al. |
| 2009/0181320 | A1 | 7/2009 | Liu et al. |

OTHER PUBLICATIONS

Jeanine Llinares, Jean-Pierre Galy, Robert Faure, Emile-Jean Vincent—Structure et reactivite des benzoxazoles: etude par resonance magnetique nucleaire du carbonne-13, published in the Can. J. Chem, 57, pp. 937-945, 1979.*
T.P. Sycheva, Z.A. Panhkina, M. N. Shchukina—Compounds with Potential Antitubercular Activity, published in the Chemistry of Heterocyclic Compounds, Jul.-Aug. 1966, vol. 2, Issue 4, pp. 377-380.*
Boswell, D.E., et al.—"The Nitrobenzo [b] thiophenes"—Mobil Research and Development Corporation—Feb. 1968—pp. 69-75.
International Search Report and Written Opinion International Application No. PCT/EP2011/050142 International Filing Date: Jan. 7, 2011.

* cited by examiner

*Primary Examiner* — Anca Eoff
(74) *Attorney, Agent, or Firm* — Kevin B. Anderson; Parashos Kalaitzis

(57) ABSTRACT

The present invention relates to a fluorine-free photoacid generator (PAG) and a photoresist composition containing the same. The PAG is characterized by the presence of an onium cationic component and a fluorine-free fused ring heteroaromatic sulfonate anionic component containing one or more electron withdrawing substituents. The onium cationic component of the PAG is preferably a sulfonium or an iodonium cation. The photoresist composition further contains an acid sensitive imaging polymer. The photoresist composition is especially useful for forming material patterns on a semiconductor substrate using 193 nm (ArF) lithography.

28 Claims, No Drawings

FLUORINE-FREE FUSED RING HETEROAROMATIC PHOTOACID GENERATORS AND RESIST COMPOSITIONS CONTAINING THE SAME

CROSS-REFERENCE TO RELATED APPLICATIONS

The present application is a divisional of and claims priority to co-pending U.S. patent application Ser. No. 12/692,961, filed Jan. 25, 2010, the entire contents of which are incorporated herein by reference.

FIELD OF THE INVENTION

This invention relates to photolithography, and more particularly to fused ring heteroaromatic photoacid generators which are fluorine-free and efficiently generate acids upon exposure to UV light. This invention is also directed to resist compositions containing the inventive fluorine-free fused ring heteroaromatic photoacid generators and methods of using the resist compositions in photolithography.

BACKGROUND OF THE INVENTION

Miniaturized electronic components such as integrated circuits are typically manufactured using photolithography technology. In a photolithography process, a photoresist layer is formed on a substrate, such as a silicon wafer. The substrate is baked to remove any solvent remained in the photoresist layer. The photoresist is then exposed through a photomask with a desired pattern to a source of actinic radiation. The radiation exposure causes a chemical reaction in the exposed areas of the photoresist and creates a latent image corresponding to the mask pattern in the photoresist layer. The photoresist is next developed in a developer solution, usually an aqueous base solution, to remove either the exposed portions of the photoresist for a positive photoresist or the unexposed portions of the photoresist for a negative photoresist. The patterned photoresist can then be used as a mask for subsequent fabrication processes on the substrate, such as deposition, etching, or ion implantation processes.

One type of photoresist employed in the prior art is a chemically amplified photoresist which uses acid catalysis. Chemically amplified photoresists have increased sensitivity to exposure energy over non-chemically amplified photoresists. A chemically amplified photoresist is especially useful when relatively short wavelength radiation is employed, such as deep UV radiation (150-315 nm wavelengths) and mid-UV radiation (350-450 nm wavelengths).

A typical prior art chemically amplified photoresist, for example, is formulated by dissolving an acid sensitive base polymer and a photoacid generator (PAG) in a casting solution. The base polymer in a chemically amplified positive photoresist typically has acid labile groups bonded to the polymer backbone. When such a photoresist is exposed to radiation, the PAG absorbs photons and produces an acid. The photo generated acid then causes catalytic cleavage of the acid labile groups. A single acid molecule generated in this manner may be capable of cleaving multiple acid labile groups on the base polymer. Thus, fewer photons are needed to render the exposed portion of the photoresist soluble in the developer solution.

Because of the relatively low intensity of a 193 nm laser source and relatively high binding energy of acid labile groups in a 193 nm photoresist, PAGs which can produce stronger Bronsted acid with high sensitivity are preferred to realize such a chemical amplification in commercial 193 nm photolithography. Fluorine-containing PAGs, such as perfluorooctyl sulfonate (PFOS) and perfluoroalkyl sulfonate (PFAS), are generally preferred PAGs in 193 nm photoresist system partially because they result in generation of strong acids.

In recent years, however, there has been a desire in the microelectronics industry to eliminate the use of perfluorinated carbons (PFCs) including PFOS and PFAS due to their detrimental effects on environment, human and animals. Thus, there is a desire to find alternative PAGs which can be used without adversely impacting the performance of lithographic processes. There has also been a desire to minimize or eliminate fluorine content in photoresist in order to improve etch resistance and to improve process latitude in high numeric aperture (NA >0.95) imaging processes. Accordingly, there is a need for new and improved fluorine-free PAGs and chemically amplified photoresist compositions that enable the substantial reduction or avoidance of fluorine content in photoresist compositions.

SUMMARY OF THE INVENTION

The present invention provides fluorine-free photoacid generators which are a viable alternative to the PFC-containing photoacid generators currently used in the industry. This invention also provides photoresist compositions containing such a fluorine-free photoacid generator that show excellent optical clarity and thermal stability and have lithographic performance equal to or better than that of photoresists having the PFC-containing photoacid generators.

In one aspect, the present invention relates to a fluorine-free photoacid generator including an onium cationic component and an anionic component having one of the following two structures:

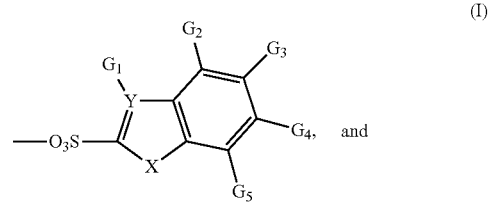

(I)

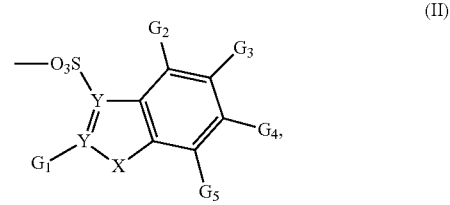

(II)

wherein:

X is selected from the group consisting of S, O and NR;

R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;

Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety.

The onium cationic component of the fluorine-free photoacid generator is preferably selected from the group consisting of sulfonium cations and iodonium cations. The onium cationic component preferably includes an aromatic moiety.

In another aspect, the present invention relates to a photoresist composition including:

(a) an acid sensitive imaging polymer; and (b) a fluorine-free photoacid generator comprising an onium cationic component and an anionic component having one of the following two structures:

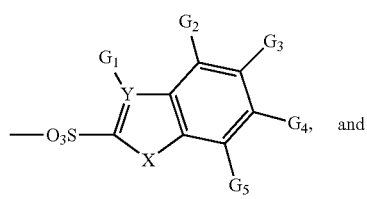

(I)

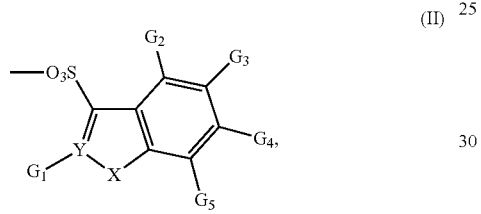

(II)

wherein:

X is selected from the group consisting of S, O and NR;

R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;

Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety.

The imaging polymer of the photoresist composition preferably has a lactone moiety. The imaging polymer preferably has a weight concentration ranging from about 1% to about 30% of the total weight of the photoresist composition. The fluorine-free photoacid generator preferably has a weight concentration ranging from about 0.5% to about 20% based on the total weight of said imaging polymer.

In still another aspect, the present invention relates to a method of forming a patterned material feature on a substrate including the steps of:

(a) providing a material layer on a substrate;

(b) forming a photoresist layer over the material layer, the photoresist comprising:

(i) an acid sensitive imaging polymer; and (ii) a fluorine-free photoacid generator comprising an onium cationic component and an anionic component one of the following two structures:

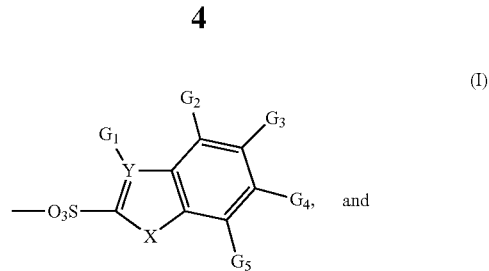

(I)

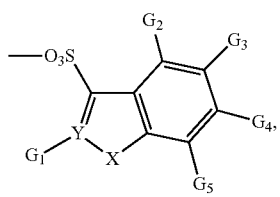

(II)

wherein:

X is selected from the group consisting of S, O and NR;

R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;

Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety;

(c) patternwise exposing the photoresist layer to radiation, thereby creating a pattern of radiation-exposed regions in the photoresist layer;

(d) selectively removing portions of the photoresist layer to expose portions of the material layer; and (e) etching or ion implanting the exposed portions of the material layer, thereby forming the patterned material feature.

The radiation of the method is preferably provided by an ArF laser.

DETAILED DESCRIPTION OF PREFERRED EMBODIMENTS

It will be understood that when an element, such as a layer, is referred to as being "on" or "over" another element, it can be directly on the other element or intervening elements may also be present. In contrast, when an element is referred to as being "directly on" or "directly over" another element, there are no intervening elements present.

The present invention provides a fluorine-free photoacid generator (PAG) which is a viable alternative to the PFC-containing photoacid generators currently used in the industry. The fluorine-free PAG is generally characterized by the presence of an onium cationic component and an anionic component having one of the following two structures:

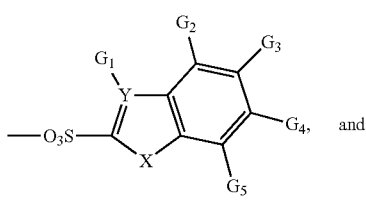
(I)

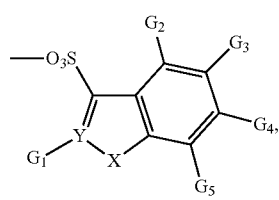
(II)

wherein:

X is selected from the group consisting of S, O and NR;

R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;

Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety.

In one embodiment of the present invention, one of $G_1$-$G_5$ is an electron withdrawing moiety. In another embodiment of the present invention, at least two of $G_1$-$G_5$ are electron withdrawing moieties. Examples of the electron withdrawing moieties suitable for the present invention include, but are not limited to, CN, NO, $NO_2$, Cl, Br, I, $SO_2Me$, and CHO. Preferably, at least one of $G_1$-$G_5$ is CN or $NO_2$.

The onium cationic component of the fluorine-free PAG is preferably a sulfonium cation or an iodonium cation. Preferably, the onium cationic component has an aromatic moiety. The aromatic structure of the cationic component generally improves the thermal stability of the resulting fluorine-free PAG. Two preferred cationic component for the present invention are:

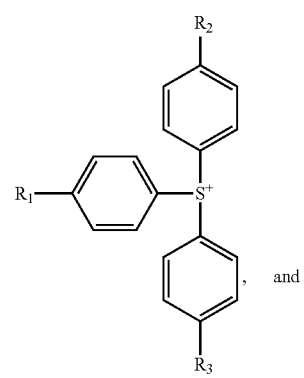
(III)

(IV)

wherein each of $R_1$, $R_2$, $R_3$, $R_4$, and $R_5$ is independently selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups. Examples of a sulfonium cation of the structure (III) are:

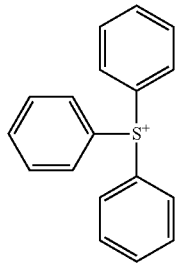
(V)

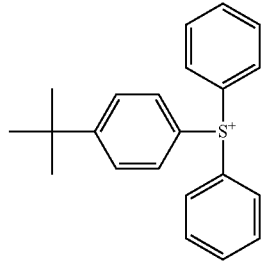
(VI)

An example of an iodonium cation of the structure (IV) is:

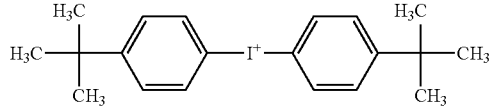
(VII)

Examples of the anionic component of structures (I) and (II) are:

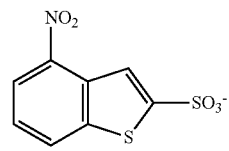
(VIII)

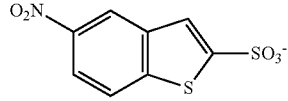
(IX)

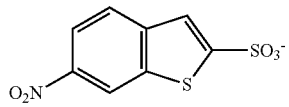
(X)

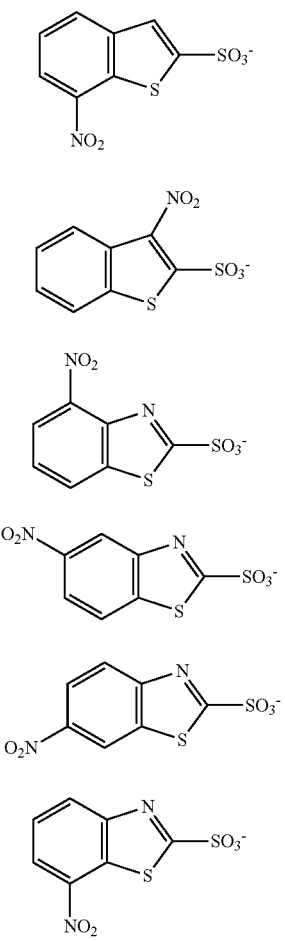

(XI)

(XII)

(XIII)

(XIV)

(XV)

(XVI)

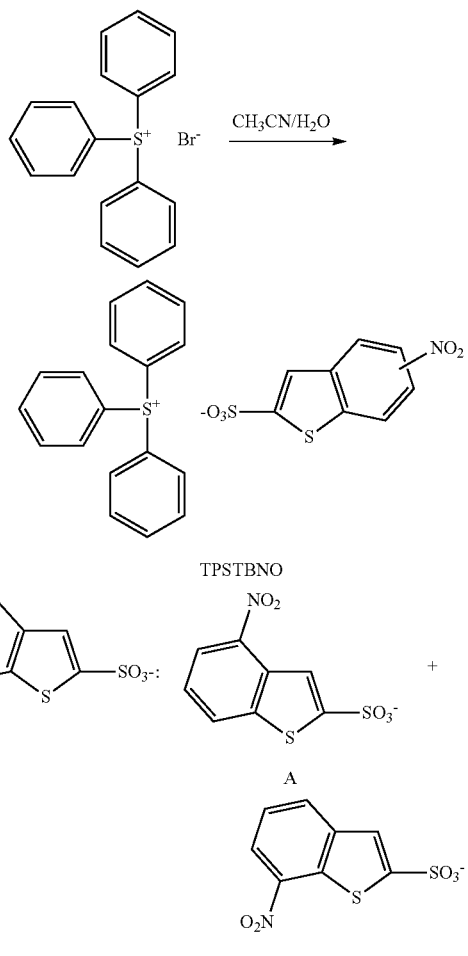

TPSTBNO (A:B = 65:35)

The invention is not limited to any specific method for synthesizing the fluorine-free PAGs of the invention. One possible synthesis route is shown in Scheme 1 below.

Scheme 1. Synthesis of fluorine-free fused-ring heteroaromatic PAGs.

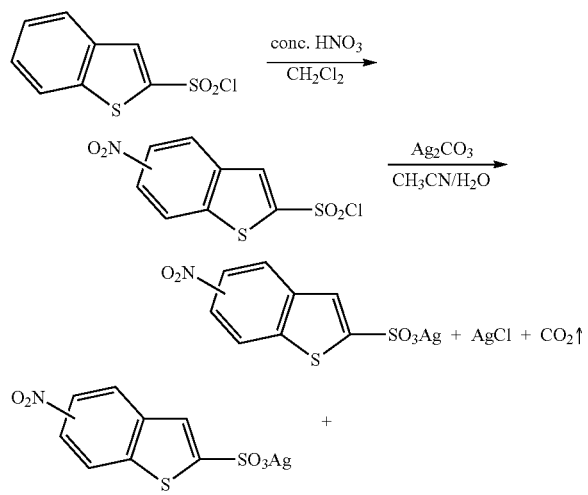

As shown in Scheme 1, in one embodiment, the synthesis of the fluorine-free fused-ring heteroaromatic PAGs starts from the nitro substitution reaction of a fused-ring heteroaromatic sulfonyl chloride, followed by a one-pot reaction to convert the nitro-substituted fused-ring heteroaromatic sulfonyl chloride to its corresponding silver sulfonate. The nitro-substituted fused-ring heteroaromatic sulfonyl chloride reacts with silver carbonate to afford the silver salt in solid phase at almost quantitative yield. The resulting silver salt then reacts with a corresponding sulfonium (or iodonium) source to afford the desired fluorine-free fused-ring heteroaromatic PAG. The chemical structures of the resulting fluorine-free fused-ring heteroaromatic PAGs can be confirmed by their NMR spectra. In the instance of synthesis of the triphenyl sulfonium mono nitro-benzo[b]thiophene-2-sulfonate (TPSTBNO) as shown in Scheme 1, the resulting PAG is a mixture of two isomers A and B with a molar ratio of 65:35.

The invention also encompasses a photoresist composition containing the fluorine-free PAGs of the present invention. The photoresist composition has an acid sensitive imaging polymer and a fluorine-free PAG having an onium cationic component and an anionic component having one of the following two structures:

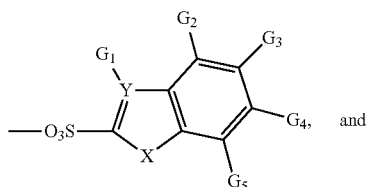

(I)

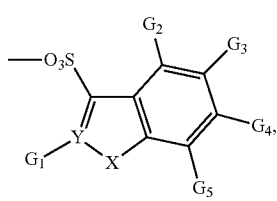

(II)

wherein:

X is selected from the group consisting of S, O and NR;

R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;

Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety.

The imaging polymer is preferably capable of undergoing chemical transformations upon exposure of the photoresist composition to UV light whereby a differential in the solubility of the polymer in either the exposed regions or the unexposed regions is created. The imaging polymer may be either a positive-tone imaging polymer or a negative-tone imaging polymer. When the imaging polymer is a positive-tone imaging polymer, it preferably includes acid sensitive side chains which can undergo catalytic cleavage in the presence of an acid generated by the inventive PAG. In such a polymer, the acid sensitivity exists because of the presence of acid sensitive side chains that are bonded to the polymer backbone. Such acid sensitive polymers including acid sensitive side chains are conventional and are well known in the art. Preferably, the imaging polymer is one suitable for use in 193 nm (ArF) lithography.

In some embodiments, the acid sensitive side chains of the acid sensitive polymers are protected with various acid labile protecting groups that are well known to those skilled in the art. For example, the acid sensitive side chains may be protected with high activation energy protecting groups such as t-butyl ester or t-butyl carbonyl groups, a low activation energy protecting group such as acetal, ketal, or silyethers, or a combination of both low and high activation energy protecting groups may also be used.

The imaging polymer of the invention preferably contains a lactone moiety, more preferably a pendant lactone moiety. Examples of imaging polymers containing lactone moieties are disclosed in US Published Patent Application No. 20060216643A1, and U.S. Pat. Nos. 7,087,356, 7,063,931, 6,902,874, 6,730,452, 6,627,391, 6,635,401 and 6,756,180. Some preferred lactone-containing monomeric units suitable for the present invention are:

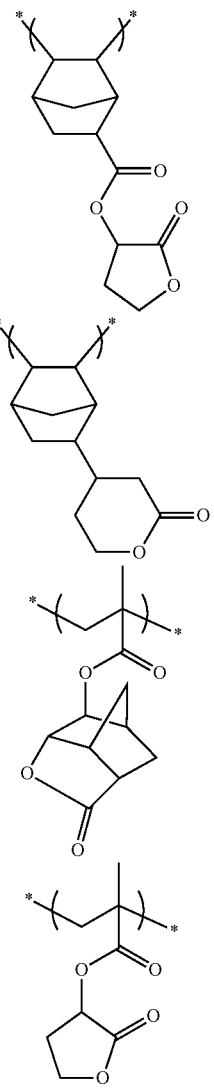

Preferred imaging polymers contain at least about 5 mole % of lactone-containing monomeric units based on the total monomeric units in the imaging polymer, more preferably about 10-50 mole %, most preferably about 15-35 mole %.

The photoresist compositions of the invention preferably contain a solvent which is capable of dissolving the acid sensitive imaging polymer. Examples of such solvents include, but are not limited to: ethers, glycol ethers, aromatic hydrocarbons, ketones, esters and the like. A solvent system including a mixture of the aforementioned solvents is also contemplated herein. Suitable glycol ethers include: 2-methoxyethyl ether (diglyme), ethylene glycol monomethyl ether, propylene glycol monomethyl ether, propylene glycol monomethylether acetate (PGMEA) and the like. Suitable aromatic hydrocarbon solvents that include: toluene, xylene, and benzene. Examples of ketones include: methylisobutylketone, 2-heptanone, cycloheptanone, and cyclohexanone. An example of an ether solvent is tetrahydrofuran, whereas ethyl lactate and ethoxy ethyl propionate are examples of ester solvents that may be employed herein.

In addition to the above components, the photoresist composition may also include other components such as photosensitizers, bases, surfactants or other additives. If desired, combinations or mixtures of these other components may be used (e.g., a photosensitizer and a base).

The optional photosensitizer is preferably one containing chromophores that are capable of absorbing irradiation in 193 nm (ArF) lithography. Illustrative examples of such compounds include, but are not limited to: 9-anthracene methanol, coumarins, 9,10-bis(trimethoxysily ethynyl) anthracene and polymers containing these chromophores.

The optional bases that can be employed in the present invention include, but are not limited to: aliphatic amines, aromatic amines, carboxylates, hydroxides, or combinations thereof and the like.

The optional surfactants that can be employed in the photoresist compositions include any surfactant that is capable of improving the coating homogeneity of the chemically amplified photoresist composition of the present invention. Illustrative examples include: fluorine-containing surfactants such as 3M's FC-430® and siloxane-containing surfactants such as Union Carbide's Silwet® series.

The photoresist compositions of the invention preferably comprise from about 1 to about 30 weight % imaging polymer, from about 50 to about 95 weight % solvent, and from about 0.1 to about 20 weight % fluorine-free PAG (the weight % of the fluorine-free PAG is based on the total weight of imaging polymer present in the composition).

When a photosensitizer is employed, it is preferably present in an amount of from about 0.001 to about 8 weight %, based on the total weight of imaging polymer. If a base is employed, the optional base is preferably present in an amount of from about 0.1 to about 5 weight %, based on the total weight of imaging polymer. When a surfactant is employed, it is preferably present in amount of from about 0.001 to about 0.1 weight %, based on the total weight of imaging polymer.

More preferably, the photoresist composition comprises from about 5 to about 20 weight % of imaging polymer, from about 80 to about 95 weight % solvent, and from about 0.5 to about 15 weight % of fluorine-free photoacid generator (based on the total weight of imaging polymer present in the composition), optionally, from about 0.01 to about 5 weight % photosensitizer, based on the total weight of imaging polymer, optionally, from about 0.1 to about 3 weight % base, based on the total weight of imaging polymer, and optionally, from about 0.001 to about 0.01 weight % surfactant, based on the total weight of imaging polymer.

Note that the amounts given above are exemplary and that other amounts of each of the above components, which are typically employed in the photolithography industry, can also be employed herein.

The present invention also encompasses a method of using the photoresist compositions of the invention to form patterned material features on a substrate. Such a method includes:

(a) providing a material layer on a substrate;
(b) forming a photoresist layer over the material layer, the photoresist comprising:
   (i) an acid sensitive imaging polymer; and
   (ii) a fluorine-free photoacid generator comprising an onium cationic component and an anionic component one of the following two structures:

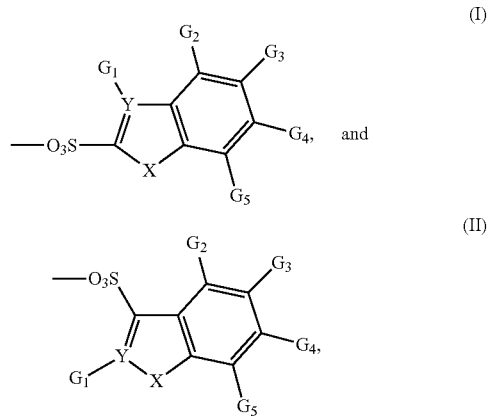

wherein:
X is selected from the group consisting of S, O and NR;
R is selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups;
Y is selected from the group consisting of C and N; and each of $G_1$-$G_5$ is selected from the group consisting of R and an electron withdrawing moiety, provided that when Y is N, $G_1$ is not present in the structure and at least one of $G_1$-$G_5$ is an electron withdrawing moiety;

(c) patternwise exposing the photoresist layer to radiation, thereby creating a pattern of radiation-exposed regions in the photoresist layer;
(d) selectively removing portions of the photoresist layer to expose portions of the material layer; and
(e) etching or ion implanting the exposed portions of the material layer, thereby forming the patterned material feature.

The substrate in the present invention is suitably any substrate conventionally used in processes involving photoresists. For example, the substrate can be silicon, silicon oxide, aluminum-aluminum oxide, gallium arsenide, ceramic, quartz, copper or any combination thereof, including multilayers. The substrate can include one or more semiconductor layers or structures and can include active or operable portions of semiconductor devices.

The material layer may be a metal conductor layer, a ceramic insulator layer, a semiconductor layer or other material depending on the stage of the manufacture process and the desired material set for the end product. The photoresist compositions of the invention are especially useful for lithographic processes used in the manufacture of integrated circuits on semiconductor substrates. The photoresist compositions of the invention can be used in lithographic processes to create patterned material layer structures such as metal wiring lines, holes for contacts or vias, insulation sections (e.g., damascene trenches or shallow trench isolation), trenches for capacitor structures, ion implanted semiconductor structures for transistors, etc. as might be used in integrated circuit devices.

In some cases, a bottom antireflective coating and/or underlayer coating (e.g., a planarizing underlayer) may be applied between the photoresist layer and the material layer. In other cases, a top antireflective coating layer may be applied over the photoresist layer. The invention is not limited to the use of antireflective reflective coatings and/or underlayer materials, nor specific compositions of those coatings or materials.

The photoresist layer may be formed by virtually any standard means including spin coating. The photoresist layer may be baked (post applying bake (PAB)) to remove any solvent from the photoresist and improve the coherence of the photoresist layer. The preferred range of the PAB temperature for the photoresist layer is from about 70° C. to about 150° C., more preferably from about 90° C. to about 130° C. The preferred range of thickness of the first layer is from about 20 nm to about 400 nm, more preferably from about 50 nm to about 300 nm.

The photoresist layer is then patternwise exposed to the desired radiation. The radiation employed in the present invention can be visible light, ultraviolet (UV), extreme ultraviolet (EUV) and electron beam (E-beam). It is preferred that the imaging wavelength of the radiation is about 248 nm, 193 nm or 13 nm. It is more preferred that the imaging wavelength of the radiation is about 193 nm (ArF laser). The patternwise exposure is conducted through a mask which is placed over the photoresist layer.

After the desired patternwise exposure, the photoresist layer is typically baked (post exposure bake (PEB)) to further complete the acid-catalyzed reaction and to enhance the contrast of the exposed pattern. The preferred range of the PEB temperature is from about 70° C. to about 120° C., more preferably from about 90° C. to about 110° C. In some instances, it is possible to avoid the PEB step since for certain chemistries, such as acetal and ketal chemistries, deprotection of the resist polymer proceeds at room temperature. The post-exposure bake is preferably conducted for about 30 seconds to 5 minutes.

After PEB, if any, the photoresist structure with the desired pattern is obtained (developed) by contacting the photoresist layer with an aqueous alkaline solution which selectively dissolves the areas of the photoresist which were exposed to radiation in the case of a positive photoresist (or the unexposed areas in the case of a negative photoresist). Preferred aqueous alkaline solutions (developers) are aqueous solutions of tetramethyl ammonium hydroxide (TMAH). The resulting lithographic structure on the substrate is then typically dried to remove any remaining developer. If a top antireflective coating has been used, it is preferably also dissolved by the developer in this step.

The pattern from the photoresist structure may then be transferred to the exposed portions of underlying material layer of the substrate by etching with a suitable etchant using techniques known in the art; preferably the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

Examples of general lithographic processes where the composition of the invention may be useful are disclosed in U.S. Pat. Nos. 4,855,017; 5,362,663; 5,429,710; 5,562,801; 5,618,751; 5,744,376; 5,801,094; 5,821,469 and 5,948,570. Other examples of pattern transfer processes are described in Chapters 12 and 13 of "Semiconductor Lithography, Principles, Practices, and Materials" by Wayne Moreau, Plenum Press, (1988). It should be understood that the invention is not limited to any specific lithography technique or device structure.

The invention is further described by the examples below. The invention is not limited to the specific details of the examples.

EXAMPLES

Example 1

Synthesis of mono nitro-benzo[b]thiophene-2-sulfonyl chloride

To a solution of benzo[b]thiophene-2-sulfonyl chloride (1.165 g, 5 mmol) in 25 mL of dichloromethane was added 3.6 mL of concentrated nitric acid (≥22.05 mol/L) dropwise, the resulting mixture was refluxed overnight and cooled to room temperature before it was poured into 20 gram of crushed ice. The organic layer was separated and the aqueous layer was extracted by 220 mL 2 dichloromethane. The organic layers were combined and dried over $MgSO_4$. Solvent was then removed by rotary evaporator. The crude product was purified by flash column chromatography with an eluent of hexane, followed by a gradient eluent of hexane/ethyl acetate (6/1-3/1) to afford 0.58 g of product (mixture of 65% of 4-nitro-benzo[b]thiophene-2-sulfonyl chloride and 35% of 7-nitro-benzo[b]thiophene-2-sulfonyl chloride).

Example 2

Synthesis of silver mono nitro-benzo[b]thiophene-2-sulfonate

To a solution of mono nitro-benzothiophene-2-sulfonate (0.5177 g, 1.86 mmol) in 50 mL of acetonitrile and 1 mL of water was added silver carbonate (0.6169 g, 2.24 mmol) in portions in darkness. The resulting suspension was stirred overnight for 9 days, until no starting material is shown on the thin layer chromatography with an eluent of hexane/ethyl acetate (1:4). The mixture was filtered through half an inch of Celite® and the solid was washed with 3×40 mL acetonitrile. The organic filtrate was combined and organic solvent was removed via rotary evaporator to dryness and thus afforded 0.668 g of viscous solid with a yield of 98.2%. The resulting compound was not purified for further reactions.

Example 3

Synthesis of triphenyl sulfonium mono nitro-benzo[b]thiophene-2-sulfonate (TPSTBNO)

To a solution of silver mono nitro-benzo[b]thiophene-2-sulfonate (0.668 g, 0.1.83 mmol) in 80 mL of acetonitrile and 4 mL of water was added a solution of triphenyl sulfonium bromide (0.6271 g, 1.83 mmol) in 35 mL of acetonitrile and 1 mL of water. The resulting mixture was stirred overnight for 3 days before it was filtered. The resulting solution was filtered though 1 inch of Celite®/aluminum oxide basic/Celite® layer and washed with 25 mL of acetonitrile and 25 mL of acetone. The organic solvent was removed via rotary evaporator and the residue was re-dissolved in 50 mL of 2-butanone, dried over magnesium sulfate over night and filtered though 1 inch of Celite®. Solvent was removed by rotary evaporator and dried over vacuum oven to dryness and thus afforded 0.71 g of product with a yield of 70%. A melting point of 243° C. was obtained with TPSTBNO in a DSC measurement (10° C./min, nitrogen 5 mL/min). No obvious decomposition up to 250° C. was observed in the DSC measurement.

Example 4

Photoresist Formulation 1

4.9967 g of a photoresist polymer consisting of 15 mol % of 2-trifluoromethanesulfonylamino methacrylate, 45 mol % of 2-methyl-2-adamantyl methacrylate and 40 mol % of 5-methacryloyloxy-2,6-norbornanecarbo-γ-lactone (S1) (20 wt % solution in PGMEA), 0.2541 g of triphenyl sulfonium nonafluorobutanesulfonate (TPSPFBuS) (19.6 wt % solution in PGMEA), 0.3092 g of N-Boc-pyrolidine (1 wt % solution in PGMEA), 5.9311 g of PGMEA and 4.4975 g of cyclohexanone were mixed and rotated overnight, filtered though 0.2 μm PTFE disc to afford formulation 1.

Example 5

Photoresist Formulation 2

5.0508 g of photoresist polymer S1 (20 wt % solution in PGMEA), 0.0467 g of TPSTBNO, 0.3057 g of N-Boc-pyrolidine (1 wt % solution in PGMEA), 6.0932 g of PGMEA and 4.4515 g of cyclohexanone were mixed and rotated overnight, filtered though 0.2 μm PTFE disc to afford formulation 2.

Example 6

Photoresist Formulation 3

3.1826 g of photoresist polymer S1 (26.75 wt % solution in PGMEA), 0.2190 g of TPSPFBuS (19.6 wt % solution in PGMEA), 0.2572 g of N-Boc-pyrolidine (1 wt % solution in PGMEA), and 14.2645 g of PGMEA were mixed and rotated overnight, filtered though 0.2 μm PTFE disc to afford formulation 3.

Example 7

Photoresist Formulation 4

7.4842 g of photoresist polymer S1 (26.75 wt % solution in PGMEA), 0.0932 g of TPSTBNO, 1.0484 g of N-Boc-2-phenyl benzimidazole (1 wt % solution in PGMEA), 30.4721 g of PGMEA and 0.5974 g of -butyrolactone were mixed and rotated overnight, filtered though 0.2 μm PTFE disc to afford formulation 4.

Physical Properties:

Thin solid films were prepared by spin-coating photoresist formulations over 5 inch silicon wafers at the spin rate of 1500 rpm for 30 seconds. The resulting films were soft baked at 110° C. for 60 seconds. The thickness, n and k were measured by VASE ellipsometry, OD values were calculated from k.

TABLE 1

Physical properties of photoresist composite thin films for 193 nm lithography.

| Formulation | PAG | Thickness (nm) | n (193 nm) | k | Es (mJ/cm$^2$) |
|---|---|---|---|---|---|
| 1 | TPSPFBuS | 180 | 1.6993 | 0.035 | 20 |
| 2 | TPSTBNO | 180 | 1.6966 | 0.039 | 35 |

Lithographic Evaluation:

For lithographic evaluation, the prepared photoresists formulation was spin-coated for 30 seconds onto an antireflective coating material layer applied on silicon wafers. In the case of 193 nm immersion lithography, a topcoat layer was applied above photoresist layer. The resist film was baked at 110 C for 60 seconds on a hotplate for 60 seconds. The wafers were then exposed to 193 nm radiation (ASML, scanner 0.75 NA, and ASML, immersion scanner 1.35 NA, respectively). The exposure pattern was an array of lines and spaces of various dimensions down to 50 nm. The exposed wafer was then post-exposure baked on a hot plate at 120 C for 60 seconds. The wafers were puddle developed by 0.263 N TMAH developer for 60 seconds. The resulting patterns of the photoresist imaging layers were examined by scanning electron microscopy (SEM). The photospeed results were obtained from the images of 150 nm line/150 nm space and 50 nm line/50 nm space, respectively.

TABLE 2

Physical properties of photoresist composite thin films for 193 nm immersion lithography.

| Formulation | PAG | Thickness (nm) | n (193 nm) | k | $E_{cd}$ (mJ/cm$^2$) | MEEF | LWR |
|---|---|---|---|---|---|---|---|
| 3 | TPSPFBuS | 120 | 1.6997 | 0.035 | 13 | 3.1 | 12.2 |
| 4 | TPSTBNO | 120 | 1.6985 | 0.039 | 28 | 3.23 | 8.4 |

While the present invention has been particularly shown and described with respect to preferred embodiments, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

What is claimed is:

1. A fluorine-free photoacid generator, said photoacid generator comprising an onium cationic component and an anionic component of formula (I):

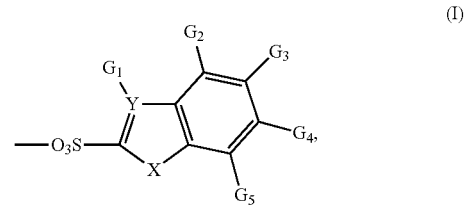

wherein:

X is O;

Y is N, $G_1$ is not present in the structure; and each of $G_2$-$G_5$ is selected from the group consisting of H; linear, branched, tertiary, or cyclic alkyl; linear, branched, tertiary or cyclic alkoxyl; unsubstituted and substituted aromatic groups; unsubstituted and substituted heteroaromatic group and an electron withdrawing moiety, provided that at least one of $G_2$-$G_5$ is an electron withdrawing moiety.

2. The photoacid generator of claim 1 wherein at least one of $G_2$-$G_5$ is an electron withdrawing moiety selected from the group consisting of CN, NO, $NO_2$, Cl, Br, I, $SO_2Me$, and CHO.

3. The photoacid generator of claim 2 wherein at least one of $G_2$-$G_5$ is selected from the group consisting of CN and $NO_2$.

4. The photoacid generator of claim 2 wherein at least two of $G_2$-$G_5$ are electron withdrawing moieties.

5. The photoacid generator of claim 1 wherein said onium cationic component is selected from the group consisting of sulfonium cations and iodonium cations.

6. The photoacid generator of claim 5 wherein said onium cationic component comprises an aromatic moiety.

7. The photoacid generator of claim 6 wherein said onium cationic component has a structure selected from the group consisting of

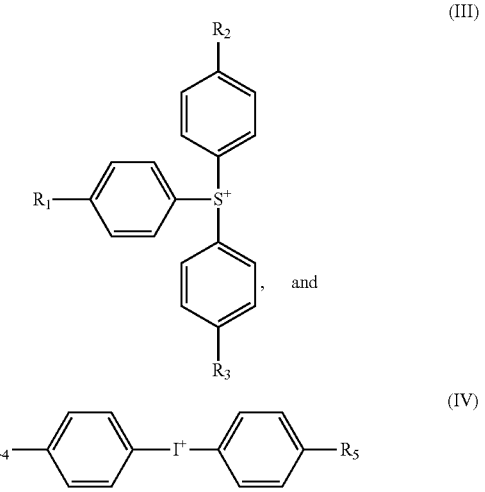

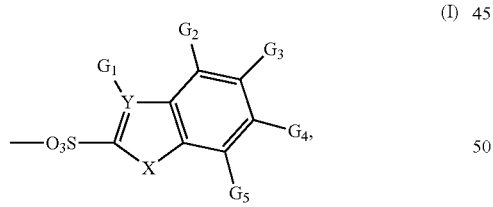

wherein each of $R_1$, $R_2$, $R_3$, $R_4$, and $R_5$ is independently selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups.

8. A photoresist composition comprising:
(a) an acid sensitive imaging polymer; and
(b) a fluorine-free photoacid generator comprising an onium cationic component and an anionic component of formula (I):

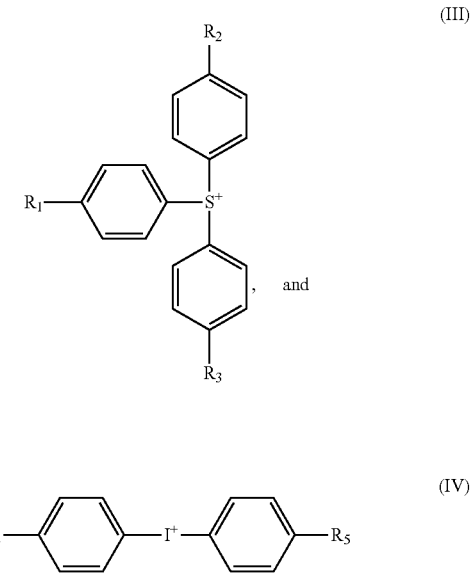

wherein:
X is O;
Y is N, $G_1$ is not present in the structure; and
each of $G_2$-$G_5$ is selected from the group consisting of H; linear, branched, tertiary, or cyclic alkyl; linear, branched, tertiary or cyclic alkoxyl; unsubstituted and substituted aromatic groups; unsubstituted and substituted heteroaromatic group and an electron withdrawing moiety, provided that when at least one of $G_2$-$G_5$ is an electron withdrawing moiety.

9. The photoresist composition of claim 8 wherein at least one of $G_2$-$G_5$ is an electron withdrawing moiety selected from the group consisting of CN, NO, $NO_2$, Cl, Br, I, $SO_2Me$, and CHO.

10. The photoresist composition of claim 9 wherein at least one of $G_2$-$G_5$ is selected from the group consisting of CN and $NO_2$.

11. The photoresist composition of claim 9 wherein at least two of $G_2$-$G_5$ are electron withdrawing moieties.

12. The photoresist composition of claim 8 wherein said onium cationic component is selected from the group consisting of sulfonium cations and iodonium cations.

13. The photoresist composition of claim 12 wherein said onium cationic component comprises an aromatic moiety.

14. The photoresist composition of claim 13 wherein said onium cationic component has a structure selected from the group consisting of

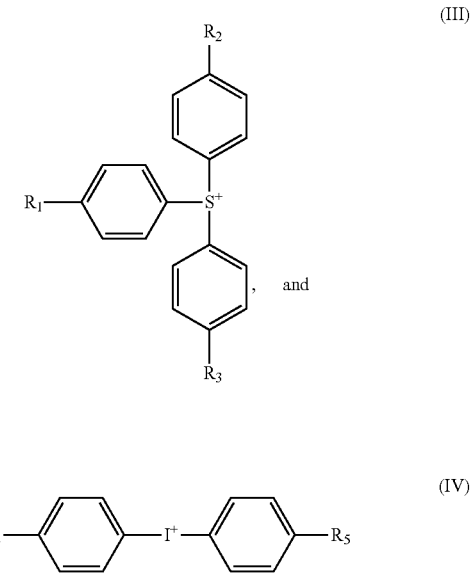

wherein each of $R_1$, $R_2$, $R_3$, $R_4$, and $R_5$ is independently selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups.

15. The photoresist composition of claim 8 wherein said imaging polymer comprises a lactone moiety.

16. The photoresist composition of claim 8 wherein said imaging polymer has a weight concentration ranging from about 5% to about 20% of the total weight of said photoresist composition.

17. The photoresist composition of claim 8 wherein said fluorine-free photoacid generator has a weight concentration ranging from about 0.5% to about 15% based on the total weight of said imaging polymer.

18. A method of forming a patterned material feature on a substrate, said method comprising:
(a) providing a material layer on a substrate;
(b) forming a photoresist layer over said material layer, said photoresist comprising:
(i) an acid sensitive imaging polymer; and
(ii) a fluorine-free photoacid generator comprising an onium cationic component and an anionic component of formula (I):

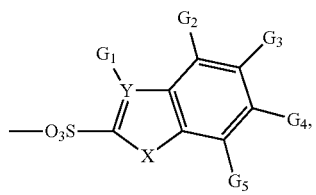

(I)

wherein:
X is O;
Y is N, G₁ is not present in the structure; and
each of G₂-G₅ is selected from the group consisting of H; linear, branched, tertiary, or cyclic alkyl; linear, branched, tertiary or cyclic alkoxyl; unsubstituted and substituted aromatic groups; unsubstituted and substituted heteroaromatic group and an electron withdrawing moiety, provided that at least one of G₂-G₅ is an electron withdrawing moiety;

(c) patternwise exposing said photoresist layer to radiation, thereby creating a pattern of radiation-exposed regions in said photoresist layer;

(d) selectively removing portions of said photoresist layer to expose portions of said material layer; and (e) etching or ion implanting said exposed portions of said material layer, thereby forming said patterned material feature.

19. The method of claim 18 wherein said radiation is provided by an ArF laser.

20. The method of claim 18 wherein at least one of the G₂-G₅ moieties is an electron withdrawing moiety selected from the group consisting of CN, NO, NO₂, Cl, Br, I, SO₂Me, and CHO.

21. The method of claim 20 wherein at least one of G₂-G₅ is selected from the group consisting of CN and NO₂.

22. The method of claim 20 wherein at least two of G₂-G₅ are electron withdrawing moieties.

23. The method of claim 18 wherein said onium cationic component is selected from the group consisting of sulfonium cations and iodonium cations.

24. The method of claim 23 wherein said onium cationic component comprises an aromatic moiety.

25. The method of claim 24 wherein said onium cationic component has a structure selected from the group consisting of

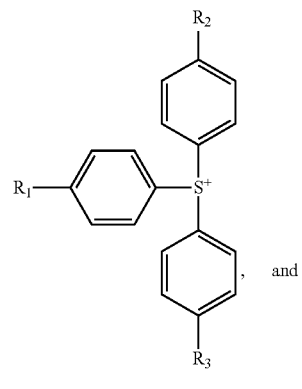

(III)

, and

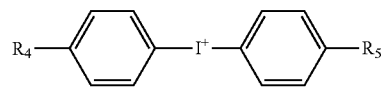

(IV)

wherein each of R₁, R₂, R₃, R₄, and R₅ is independently selected from the group consisting of H; linear, branched, tertiary, or cyclic alkyl; linear, branched, tertiary or cyclic alkoxyl; unsubstituted and substituted aromatic groups; and unsubstituted and substituted heteroaromatic groups.

26. The method of claim 18 wherein said imaging polymer comprises a lactone moiety.

27. The method of claim 18 wherein said imaging polymer has a weight concentration ranging from about 5% to about 20% of the total weight of said photoresist composition.

28. The method of claim 18 wherein said fluorine-free photoacid generator has a weight concentration ranging from about 0.5% to about 10% based on the total weight of said imaging polymer.

* * * * *